United States Patent [19]

Watson et al.

[11] Patent Number: 4,777,962

[45] Date of Patent: Oct. 18, 1988

[54] METHOD AND APPARATUS FOR DISTINGUISHING CENTRAL OBSTRUCTIVE AND MIXED APNEAS BY EXTERNAL MONITORING DEVICES WHICH MEASURE RIB CAGE AND ABDOMINAL COMPARTMENTAL EXCURSIONS DURING RESPIRATION

[75] Inventors: Herman Watson, Miami; Marvin A. Sackner, Miami Beach; Anne S. Belsito, Miami, all of Fla.

[73] Assignee: Respitrace Corporation, Miami Beach, Fla.

[21] Appl. No.: 15,052

[22] Filed: Feb. 17, 1987

Related U.S. Application Data

[63] Continuation-in-part of Ser. No. 861,327, May 9, 1986, abandoned.

[51] Int. Cl.$^4$ .............................................. A61B 5/08
[52] U.S. Cl. ..................................... 128/716; 128/721
[58] Field of Search ................ 128/716, 719, 721–723, 128/725–728, 774, 204.23

[56] References Cited

U.S. PATENT DOCUMENTS

| | | | |
|---|---|---|---|
| 4,258,718 | 3/1981 | Goldman | 128/725 |
| 4,267,845 | 5/1981 | Robertson, Jr. et al. | 128/721 |
| 4,269,195 | 5/1981 | Itoh | 128/723 |
| 4,373,534 | 2/1983 | Watson | 128/721 |
| 4,648,407 | 3/1987 | Sackner | 128/721 |
| 4,686,999 | 8/1987 | Snyder et al. | 128/716 |

FOREIGN PATENT DOCUMENTS

| | | |
|---|---|---|
| 78677 | 5/1983 | European Pat. Off. ............ 128/716 |
| 7908206 | 6/1981 | Netherlands ..................... 128/716 |
| 1472650 | 5/1977 | United Kingdom . |
| 2061735 | 5/1981 | United Kingdom . |
| 2142246 | 1/1985 | United Kingdom . |

OTHER PUBLICATIONS

Konno, K., Mead J., Measurement of the Separate Volume Change, etc. J. Appl. Physiol. 1967; 22: 407–422.
Tobin M. J., et al., Breathing Abnormalities During Sleep, Archives of Internal Medicine 1983; 143: 1221–1228.
Sackner, M. A., Sleep and Arousal Disorders, Guides to the Evaluation of Permanent Impairment, 2d Ed., 1984; 229–39.
Catley, D. M., et al., Pronounced, Episodic Oxygen Desaturation, etc., Anesthesiology 1985; 63: 20–28.
Staats, B. A., et al., Chest Wall Motion in Sleep Apena, Am. Rev. Respir. Dis. 1984; 130:59–63.
Tobin, M. J., et al., Breathing Patterns—1. Normal Subjects Chest 1983; 84: 202–05.
Tobin, M. J., et al., Breathing Patterns—2. Diseased Subjects, Chest 1983; 84: 286–294.

Primary Examiner—Lee S. Cohen
Assistant Examiner—David Shay
Attorney, Agent, or Firm—Schecter, Brucker & Pavane

[57] ABSTRACT

An apparatus and method for distinguishing between different types of apneic episodes. The method includes measuring a new index, TCD/VT, and measuring the phase relation between the abdominal and rib cage contributions to total respiration volume. The episode is classified as central, obstructive or mixed based on the value of TCD/VT and the phase relation.

12 Claims, 18 Drawing Sheets

METHOD AND APPARATUS FOR DISTINGUISHING CENTRAL OBSTRUCTIVE AND MIXED APNEAS BY EXTERNAL MONITORING DEVICES WHICH MEASURE RIB CAGE AND ABDOMINAL COMPARTMENTAL EXCURSIONS DURING RESPIRATION

This application is a continuation-in-part of application Ser. No. 861,327, filed May 9, 1986, now abandoned.

BACKGROUND OF THE INVENTION

A. Technical Field

This invention pertains to methods and apparatus for detecting and distinguishing respiration disorders, especially apneas.

B. Background Art

In 1967, Konno and Mead demonstrated that motion of the respiratory system can be closely approximated by two degrees of freedom. (Konno K., Mead J., Measurement of the Separate Volume Change of Rio Cage and Abdomen During Breathing, J. Appl Physiol. 1967; 22: 407-22) They found that volume change at the mouth (open system) is equal to the sum of the volume change of the rib cage (RC) and abdominal (AB) compartments such that Volume=RC+AB. The occlusion of the mouth or airway (closed system), produced one degree of freedom of motion with any volume change of RC equal and opposite in magnitude to that of AB. This work provided a basis for calibrating devices which monitored changes in RC and AB volume, e.g. linear displacement transducers, magnetometers and the respiratory inductive plethysmograph. In particular, the subject breathed against a valve which was occluded, and then at constant lung volume gently made voluntary movements to shift volume from RC to AB and vice-versa. This "isovolume maneuver" was then used to set the electrical gains of the RC and AB transducers such that the two signals, which are opposite in direction during the maneuver, become equal in amplitude. Once this was accomplished, the subject breathed against an external calibrated volumetric device, such as a spirometer or integrated pneumotachygraph system, whereupon the gain factors of the RC and AB transducers were set to render the SUM (RC+AB) equal to the actual tidal volume reading at the external calibrated volumetric device.

The awareness of the consequences of the isovolume maneuver has also been used to distinguish central apneas from obstructive apneas. These events, which occur during sleep, drowsiness and with narcotic overdose, are well recognized as clinical entites, viz., Cheynes-Stokes Respiration, Obstructive Sleep Apnea Syndrome and Sudden Infant Death Syndrome (SIDS). These disorders can be detected by visual inspection of the waveforms of RC, AB and the SUM of these two compartmental displacements during the apnea. (Tobin M. J., Cohn M. A., Sackner M. A., Breathing Abnormalities During Sleep, Arch. Intern. Med. 1983; 143: 1221-28; Sackner, M. A., Sleep and Arousal Disorders, AMA Guides to Impairment, 2d Ed., 1984; 229-39; Catley D. M., Thornton C., Jordan C., Lehane J. R., Royston D., Jones J. G., Pronounced, Episodic Oxygen Desaturation in the Post-Operative Period: Its Association with Ventilatory Pattern and Analgesic Regimen, Anesthesiology 1985; 63: 20-8; Staats B. A., Bonekat H. W., Harris C. D., Offord K. P., Chest Wall Motion in Sleep Apnea, Am. Rev. Respir. Dis. 1984; 130: 59-63). In central apnea, the respiratory center in the brain fails to command the respiratory muscles to contract and no movements appear on the RC, AB and SUM recordings. Obstructive apneas take place when the tissues of the throat region (upper airway) come into contact with each other so that no air can flow through the mouth and nose despite respiratory muscle efforts. This clinical entity of obstructive apnea is analogous to the isovolume maneuver in that the RC and AB compartments show equal or nearly equal and opposite displacements with the SUM depicting zero or nearly zero displacement. The failure to achieve zero displacement on the SUM signal can result from imperfect initial calibration of the external monitoring device, difference between RC and AB volume-motion coefficients during sleep compared to the waking state when initial calibration was carried out, and thoracic gas compression as the result of vigorous respiratory muscle efforts to overcome the upper airway obstruction. Mixed apneas are a combination of central and obstructive apneas during a single event.

Obstructive apneas can usually be recognized from their appearance on the analog recordings. It should be noted that the diagnosis of obstructive apnea can be made with greater confidence if airflow or volume is measured at the mouth and nostrils, but application of transducers at these orifices is often unsatisfactory because of poor subject cooperation and cumbersome application. Further, in up to 15% of obstructive apneas, displacements on the RC, AB and SUM recordings may be almost imperceptible, and greater confidence in distinguishing central from obstructive apneas is achieved by recording intrapleural pressure swings during the event with an intraesophageal balloon catheter or a surface inductive plethysmographic transducer (such as disclosed in co-pending commonly assigned application Serial No. 789,350) fixed to the skin of the suprasternal fossa. (Tobin M. J., Cohn M. A., Sackner M. A., Breathing Abnormalities During Sleep, Arch. Intern. Med. 1983; 143: 1221-28). However, the esophogeal balloon catheter is an invasive, unpleasant procedure for the subject while the non-invasive surface inductive plethysmograph requires close observation during the recording period due to changes in its electrical gain as a result of changes in neck position.

The detection and differentiation among apneic/-hypopneic events depends upon the following. First, the SUM recording from the RC and AB transducers must fall below an empirically determined minimal acceptable volume. Although theoretically the SUM during an apneic event should be equivalent to zero to diagnose apnea, this value cannot be restricted to zero in clinical practice. Even in central apneas, rapid, small changes in volume may occur as a result of the heartbeat which causes gas compression and rarefication within the thorax, and slow drifts may take place because of respiratory gas exchange and shifts of blood volume within the RC and AB during the central apneic event. Furthermore, if the volume to define an apnea is considered as zero, then obstructive apneas will be underestimated because small deflections of the SUM recording as a result of respiratory muscle efforts will occur as mentioned above. Finally, if the minimal acceptable volume is made zero, then minor fluctuations in the waveform within an unimpeded normal breath could be interpreted as breaths by devices, e.g. computers, which generally detect breaths by trough and peak detection. With the potential of small artifactual breaths within the true breath period, the respiratory frequency would be spuriously overestimated. For adults whose normal values for tidal breathing range from 200 to 550 ml (Tobin M. J., Chadha T. S., Jenouri G., Birch S. J., Gazeroglu H. B., Sackner M. A., Breathing Patterns—Normal Subjects, Chest 1983; 84: 202-5), one can arbitrarily denote a minimal acceptable volume as 100 ml or any other appropriate value as empirically determined.

Therefore, an apnea is defined as a period where the SUM tracing falls and stays below the minimal acceptable volume for a defined period of time. Essentially, it can be considered as a prolonged expiration, viz. from the start of expiration to the moment of inspiration. In sleep disorder centers, this time is typically taken as a duration of at least 10 seconds from the point at which zero expiratory flow begins until inspiratory flow begins. This time interval can be shortened or lengthened according to criteria formulated by the observer. A hypopneic event is typically defined as a decrease in tidal volume from a predetermined baseline, e.g., 45% of the mean baseline tidal volume of some other valve chosen by the observer.

When the apnea is detected from the SUM criteria, visual observation of the analog recordings of the RC and AB compartments provide information as to whether the event has a central, obstructive or mixed basis. In patients with Obstructive Sleep Apnea Syndrome, scoring of events can be time-consuming since in severe disease as many as 500 events occur during an 8 hour period. Furthermore, a great deal of paper weighing several pounds is required to record the analog tracings for visual inspection. There are different types of apneas having different causes. Further, hypopneic events may also take place, the latter being a decrease in tidal volume predetermined from a baseline, e.g. 45% of the mean baseline tidal volume or some other arbitrary value chosen by the observer.

In view of the foregoing, it is an object of the present invention to provide an improved method and apparatus for distinguishing among central, obstructive and mixed apneas and hypopneas.

It is a further object to utilize, as part of such improved method and apparatus, conventional devices which monitor two degrees of freedom of motion during respiration, such as a respiratory inductive plethysmograph.

DISCLOSURE OF THE INVENTION

The invention is a method and apparatus for automatically detecting and differentiating among apneic/hypopneic events. The invention relies upon two parameters, viz. (1) Total Compartmental Displacement/Tidal Volume (TCD/VT), and (2) Phase Relation (PR). It has been found that by recording these parameters during an apneic/hyponeic event and comparing same with empirically derived reference values, apneic events can be differentiated and distinguished from each other and from hypopneic events. Additional confidence in distinguishing among central obstructive and mixed apneas can be achieved by monitoring, as with surface inductive plethysmography, (co-pending commonly assigned application Ser. No. 789,350), suprasternal fossa movements resulting from changes in intrapleural pressure.

Total Compartmental Displacement/Tidal Volume (TCD/VT) is an extension of a previously reported index, Maximum Compartmental Amplitude/Tidal Volume (MCA/VT), which has been utilized to express synchronous or asynchronous movements betweeen RC and AB compartments during tidal breathing while monitoring with devices based upon measuring two degrees of freedom for respiratory system movements (Tobin M. J., Chadha T. S., Jenouri G., Birch S. J., Gazeroglu H. B., Sackner M. A., Breathing Patterns—Normal Subjects, Chest 1983; 84: 202-5; Tobin M. J., Chadha T. S., Jenouri G., Birch S. J., Gazeroglu H. B., Sackner M. A., Breathing Patterns—Diseased Subjects, Chest 1983; 84: 286-94). These devices include the respiratory inductive plethysmograph and others in which one transducer is placed upon the RC compartment and another on the AB compartment, such as magnetometers, strain gauges and the bellows pneumograph. It excludes the impedance pneumogram in which the transducer is placed only upon the rib cage.

MCA/VT is determined by adding the absolute peak to trough values of the RC and AB displacements irrespective of their timing relative to the SUM (VT) and then dividing by the SUM (VT). In normal subjects in whom all three signals are generally in phase with respect to the trough and peak value over a breath, the value of MCA/VT ranges from 1.00 to 1.10, but in patients with pulmonary disease this value is often exceeded because the trough and peaks of the RC and AB might be out of phase with the SUM (VT) signal (Tobin M. J., Chadha T. S., Jenouri G., Birch S. J., Gazeroglu H. B., Sackner M. A., Breathing Patterns—Normal Subjects, Chest 1983; 84: 202-5; Tobin M. J., Chadha T. S., Jenouri G., Birch S. J., Gazeroglu H. B., Sackner M. A., Breathng Patterns—Diseased Subjects, Chest 1983; 84: 286-94). Further, MCA/VT is not useful during apneas where peak detection of the SUM (VT) signal is impossible.

TCD/VT is calculated during breathing by taking the derivative of the entire waveforms for the RC, AB and SUM (VT) displacements. The absolute values of the derivative signals are then integrated on a breath-by-breath basis. The integrals of the absolute values of the derivative of the RC and AB signals are added together (total compartmental displacement) and divided by the SUM (VT) to give the index TCD/VT. The normal value for TCD/VT of 1.00-1.20 is slightly higher than MCA/VT which places a lower limit on the degree of asynchrony between RC and AB. When apnea discrimination in accordance with the invention is, as preferred, carried out on a computer, TCD/VT is multiplied by 10 to eliminate the decimal point as a matter of convenience.

When an apnea is detected as indicated by a fall in the SUM (VT) below a minimal acceptable breath volume, TCD/VT is computed by treating the entire apneic period as a single breath. The small oscillations often present on the SUM signal as a result of cardiogenic rarefication and compression of thoracic gas, imperfect setting of the gains of RC and AB transducers from the calibration procedure, and compression and rarefication of thoracic gas volume by respiratory muscle efforts are not considered as peaks and troughs. In contrast to MCA/VT, peak detection is unnecessary for computation of TCD/VT. It has been found that when TCD/VT×10 exceeds 25, this suggests an obstructive or mixed apnea, whereas values near 10 suggest a central basis. Intermediate values of TCD/VT can only be interpreted if the Phase Relation (PR) is also known, as is more fully discussed below.

Phase Relation (PR) is determined only during apnea and indicates whether RC and AB displacements are moving in the same or opposite directions as indicated by a comparison or algebraic signs between a moving window derivative of preferably twenty-one sample points, preferably sampled at a rate of 60 samples per second. The derivative for each window is calculated in accordance with the technique described in Description of a Computer Program for Analysis of the Forced Expiratory Spirogram, Ayers, et al., Computers and Biomedical Research, Academic Process, Vol. 2, No. 2, 207-219, 1969. Preferably the derivative signal is then subjected to truncation. Utilizing twenty-one sample points and truncating eliminates spurious changes of sign due to values caused by a slow rate of RC and AB displacement. Truncating also renders the numerical values manageable, i.e. prevents overflow when, as is preferred, calculations are carried out by a computer. Presently, truncating is accomplished by dividing by 512 ($2^9$). The number of values in phase (same sign for RC and AB) is divided by the total number of samples; this value is preferably multiplied by 100 to convert PR to a percettage value as a matter of convenience. PR values which approach 100 indicate that the RC and AB compartments are moving in phase and those approaching zero indicate an out of phase relation. It has been found that central apneas are associated with high values of PR, obstructive apneas with low values, and mixed apneas with intermediate values.

In conjunction with TCD/VT, PR helps to distinguish among central, obstructive and mixed apneas particularly at TCD/VTx10 values below 25 as more fully explained below. In central apneas, TCD/VTx10 can exceed 10 because of upgoing or downgoing drifts of RC and/or AB signals as a result of respiratory gas exchange and throacic blood volume shifts during the apneic event, but under these circumstances PR exceeds 50, also as more fully explained below.

While, in many cases, it has been found that apneas can be classified based on numeric values of TCD/VT and PR, in other cases this technique has not proved sufficient for accurate apnea discrimination. For example, in one analysis with a large number of patients having sleep-related breathing disorders, obstructive and mixed apneas could not be clearly differentited, and discrimination as between central and obstructive apneas was accurate in only approximately 75% of events.

Accordingly, in accordance with a further improved technique for discrimination among the various types of apneas, i.e. central, obstructive and mixed, TCD as well as the SUM (VT) of the rib cage (RC) and abdominal (AB) excursions during the apneic event are displayed in a compressed graphic plot, for example, as hard copy (e.g. on a line printer) or on a video display. The termination of the apneic event may be indicated on the compressed graphic plot in any suitable fashion, though preferably it is indicated by a first numerical value representing PR expressed as a percentage for the entire apneic event and a second numerical value indicating the duration of the apneic event in seconds.

When TCD and SUM (VT) are displayed in accordance with this technique, apneic events may be accurately discriminated. In particular, when the SUM (VT) and TCD lines are either superimposed or parallel and slightly displaced from each other, a purely central apnea is indicated. The displacement, if any, between the SUM (VT) and TCD lines during central apneas results from rounding-off errors in the computer calculations. Typically, central apneas are accompanied by PR ranges from 98 to 99%.

In obstructive apneas, the SUM (VT) line is horizontal or near horizontal and the TCD line rises upwardly and away from the SUM (VT) line as a function of the respiratory efforts during the obstructive apneic event. The greater the respiratory efforts, i.e. the larger the RC and AB excursions, the steeper the rise of the TCD line away from the SUM (VT) line. The TCD line is also affected by the number of respiratory efforts, i.e., the larger the number of respiratory efforts, the steeper the rise of the TCD line. The PR for an obstructive event is typically less than 97%.

In mixed apneas, there is a combination of central and obstructive components. Typically, mixed apneas begin with a central apnea component and terminate with a obstructive component, although variations do occur. In the compressed graphic plot, mixed apneas are depicted as a combination of plots indicative of central and obstructive apneas, viz, a horizontal TCD line for the central apneic component and an upward sloping TCD line for the obstructive component. PR for mixed apneic events is generally less than 97%.

It should be noted that even with this technique, obstructive apneas characterized by minimal obstructive effort can be misinterpreted as central apneas. This is so because computations of TCD are conditioned to exclude cardiogenic oscillations, i.e. heart beat deflections transmitted from the RC and AB to the respiratory inductive plethysmograph or other external monitoring device. Consequently, if the amplitude of the respiratory efforts during an obstructive event approaches the amplitude of the cardiogenic oscillations, TCD is considered as zero. As noted in a paper on breathing abnormalities during sleep, Tobin et al., Breathing Abnormalities During Sleep, Arch. Internal Medicine, 143:1221-1228, 1983, if analog waveforms do not exhibit significant oscillations on visual inspection during apneic events, central apneas cannot be discriminated with certainty from obstructive apneas with minimal respiratory efforts, unless an independent measure of respiratory efforts is recorded. As noted earlier, the latter may be accomplished with an intraesophageal balloon catheter or a surface inductive plethysmograph transducer placed on the skin of the suprasternal fossa region of the neck. Both techniques detect swings of intrapleural pressure indicating respiratory efforts during an obstructive event. In the case of a central apnea, no deflections will be recorded by these devices.

It has been found that visual inspection of the compressed graphic plot, as contrasted with the classification of apneas based solely on numerical values for TCD/VT and PR, results in more accurate discrimination among the various types of apneic events, viz, central, obstructive and mixed.

DETAILED DESCRIPTION

Figure 1:
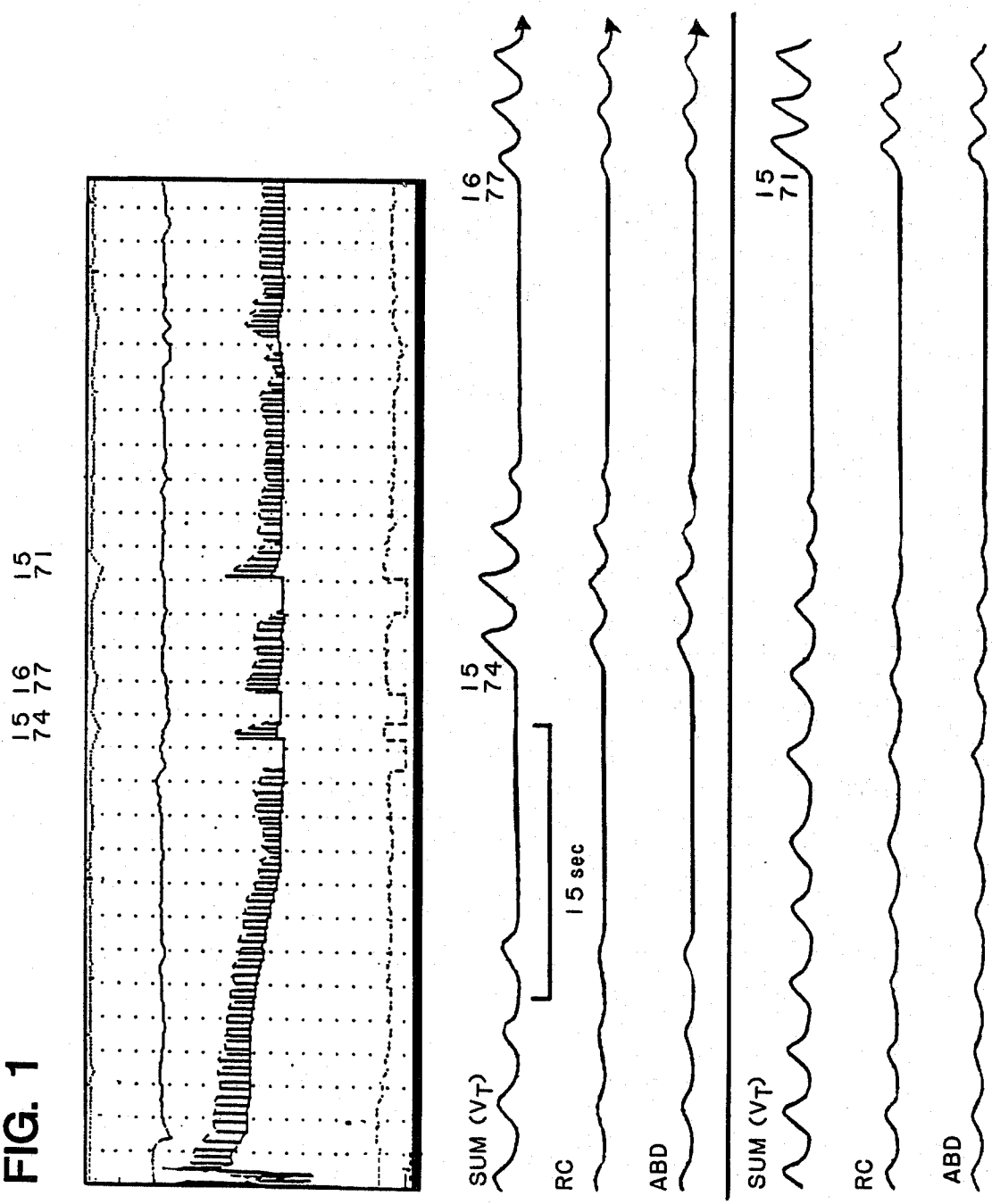
FIG. 1 illustrates tracings confirming accurate detection of central apnea in acccrdance with the present invention.

The first portion of this description pertains to the method and apparatus of the present invention for discriminating apneas by comparing measured values of TCD/VT and PR with empirically derived reference values (FIGS. 1-5). The latter portion of this description is devoted to the method and apparatus in accordance with the pesent invention for discriminating among apneic events by visual inspection of compressed graphic plot lines for TCD and SUM (VT) (FIGS. 6-18).

One hundred twelve central, obstructive and mixed apneas in seven patients undergoing clinical polysomography and 133 such events simulated by six normal volunteers were analyzed. TCD/VT and PR values as calculated from a Z80A based microprocessor system (RESPIGRAPH TM & RESPISOMNOGRAPH TM, marketed by Nims, Inc., Miami Beach, Fla.) for each event were matched to a polypgraphic recording of the SUM (VT), RC and AB waveforms during the event. Such a system is diagrammatically illustrated in FIG. 18 which shows a pair of band-type transducers 12, 14 disposed about the rib cage and abdomen, respectively, of a subject 16 for measuring the rib cage and abdominal contributions to total respiration volume. Each transducer 12, 14 incorporates a generally sinusoidal conductor 18, 20 disposed on a stretchable base 22, 24 such that expansions and contractions of the rib cage and abdomen result in changes in the inductance of the conductors 18, 20, respectively. The foregoing is in accordance with the well-known technique of respiratory inductive plethysmography. The inductance changes, after conversion to corresponding voltage changes, are processed by the microprocessor based system 26 for calculating TCD/VT, SUM (VT) AND PR. The waveforms of these parameters may then be displayed, as on a printer 28.

In accordance with the invention it has been determined that apneas can be differentiated according to the following criteria:

| TCD/VT (× 10) | PR (× 100) | Type of Apnea |
|---|---|---|
| about 10–about 15 | > about 50 | Central |
|  | ≦ about 50 | Mixed |
| about 16–about 19 | > about 50 | Central |
|  | about 40–about 49 | Mixed |
|  | < about 39 | Obstructive |
| about 20–about 25 | ≧ about 55 | Central |
|  | < about 55 | Mixed or Obstructive |
| ≧ about 25 | > about 60 | Central |
|  | about 40–about 59 | Mixed |
|  | < about 39 | Obstructive |

In this schema, two of the apneas were misdiagnosed in 112 patient apneas (these were mixed apneas with the TCD/VT and PR criteria of central apneas). Of the 133 simulated apneas by the normal volunteers, 1 obstructive apnea had criteria for central apnea; 2 mixed apneas criteria for obstructive; and 1 mixed apnea criteria for a central apnea. Thus, for the 245 events, a confirmed diagnosis as determined by the above criteria showed an accuracy of 98%.

In hypopneas, only TCD/VT is computed. Values less than or equal to 1.9 suggest a central basis and those greater than 2.0 an obstructive basis.

SPECIFIC EXAMPLES

Central Apnea

FIG. 1 is a recording obtained from a sleeping patient with excessive daytime somnolence. The top panel represents a compressed 10 minute plot of information obtained with the RESPISOMNOGRAPH Z80A based microprocessor system mentioned above which clllects and processed data from the respiratory inductive plethysmograph, pulse oximeter and activity monitor. The uppermost tracing is a continuous recording of arterial oxygen saturation (% $O_2$) from a pulse oximeter. The next lower tracing represents the heart rate in beats/min (HR) from the pulse oximeter. The vertical lines of the middle tracing indicate breath-by-breath tidal volumes as detected by the respiratory inductive plethysmograph. Total Compartment Displacement (TCD) is the hatched line at the top of the vertical lines. The end expiratory lung volume is the solid line at the base of the vertical lines. The respiratory inductive plethysmograph was calibrated using known qualitative calibration techniques, and the values are qualitative with the space between two vertical tick marks representing the tidal volume as 100% of the baseline value. The lowermost tracing indicates the breath-by-breath percent contribution of the rib cage displacement to the tidal volume (% RC). During any apneic event, this value is arbitrarily adjusted to zero to avoid infinity calculations. Above the plots are digital indices which also reflect the termianticn of the apneic event. The upper number is TCD/VT and the lower number is the Phase Relation (PR).

The middle and bottom panels of FIG. 1 are polygraphic recordings from the respiratory inductive plethysmograph for SUM (VT), RC (rib cage) and AB (abdomen) as taken during the apneic events shown in the upper panel. The events corresponding to the indices printed out from the RESPISOMNOGRAPH TM (upper panel) are all central apneas as indicated by the absence of movement on all three recordings in the lower panels, to which the indices were added manually for ease of reference. The indices properly classified the apneas as central apneas as indicated by the numerical values of TDC/VT-PR of 15-74, 16-77 and 15-77, respectively.

Obstructive Apnea

Figure 2:
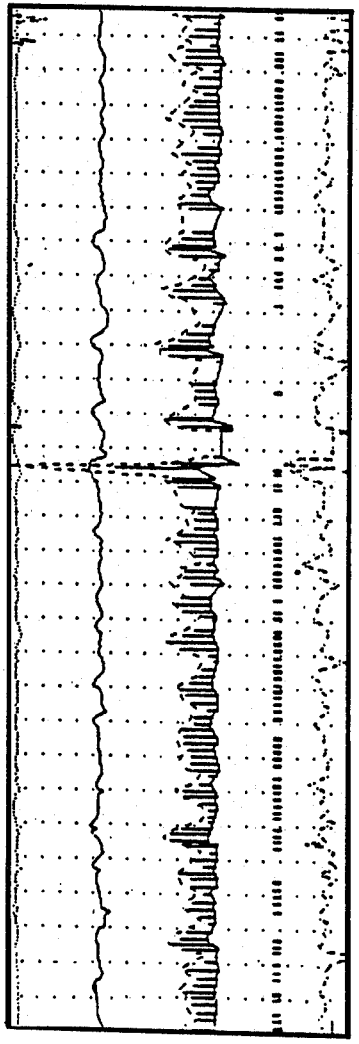
FIG. 2 illustrates tracings confirming accurat detection of obstructive apnea in accordance with the present invention.
Figure 2:
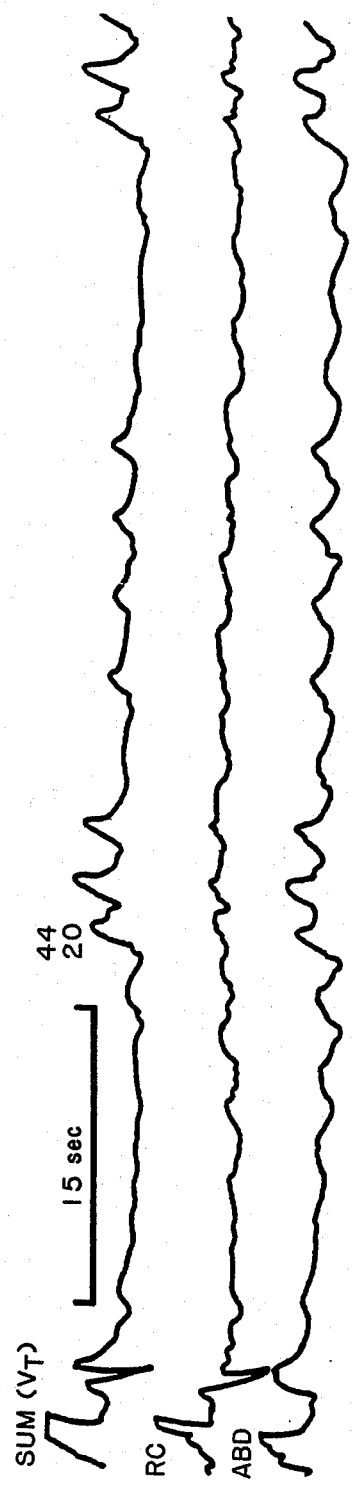

FIG. 2 is a recording obtained from a sleeping patient with excessive daytime somnolence. The top panel represents a compressed 10 minute plot from the RESPISOMNOGRAPH TM. The legend designations for the tracings in this plot are the same as for FIG. 1. In addition to the tracings seen in FIG. 1, the vertical discontinuous lines between the tidal volume and % RC plots indicate snores recorded from a microphone placed on the skin of the throat. An obstructive apnea is denoted by a TCD/VT of 44 and PR of 20. The out-of-phase movements of RC and ABD with minimal deflections on the SUM (VT) waveform are seen in the panel below. This is terminated by a cluster of three breaths nearly in phase.

Central Apnea

Figure 3:
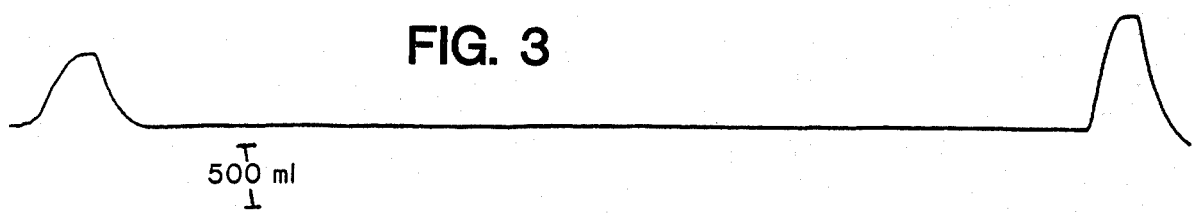
FIG. 3 is a polygraphic recording further illustrating the detection of central apnea in accordance with the present invention.
Figure 3:
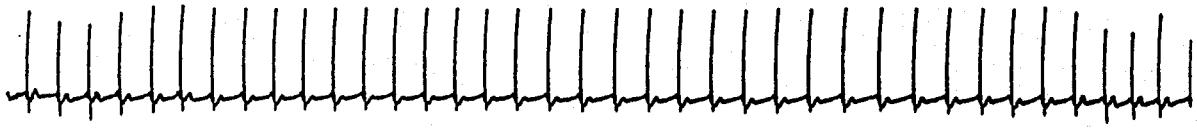
Figure 3:

FIG. 3 is a polygraphic recording from a simulation carried out by a normal volunteer. The top tracing is the movement of air volume at the mouth monitored by spirometry (SP). EKG is the electrocardiogram and IP denotes the impedance pneumogram, a device which monitors breathing with only one degree of freedom, i.e. changes in the rib cage (RC) dimension only. The lower three waveforms derived form the analog outputs of the RESPIGRAPH TM, SUM(VT), RC (rib cage), AB (abdomen), and also SP show no deflections during the central apnea simulation. The TDC of 18 and PR of 66 are consistent with this diagnosis The impedance pneumogram shows cardiac pulsations but no significant evidence of respiratory movement.

Obstructive Apnea

Figure 4:
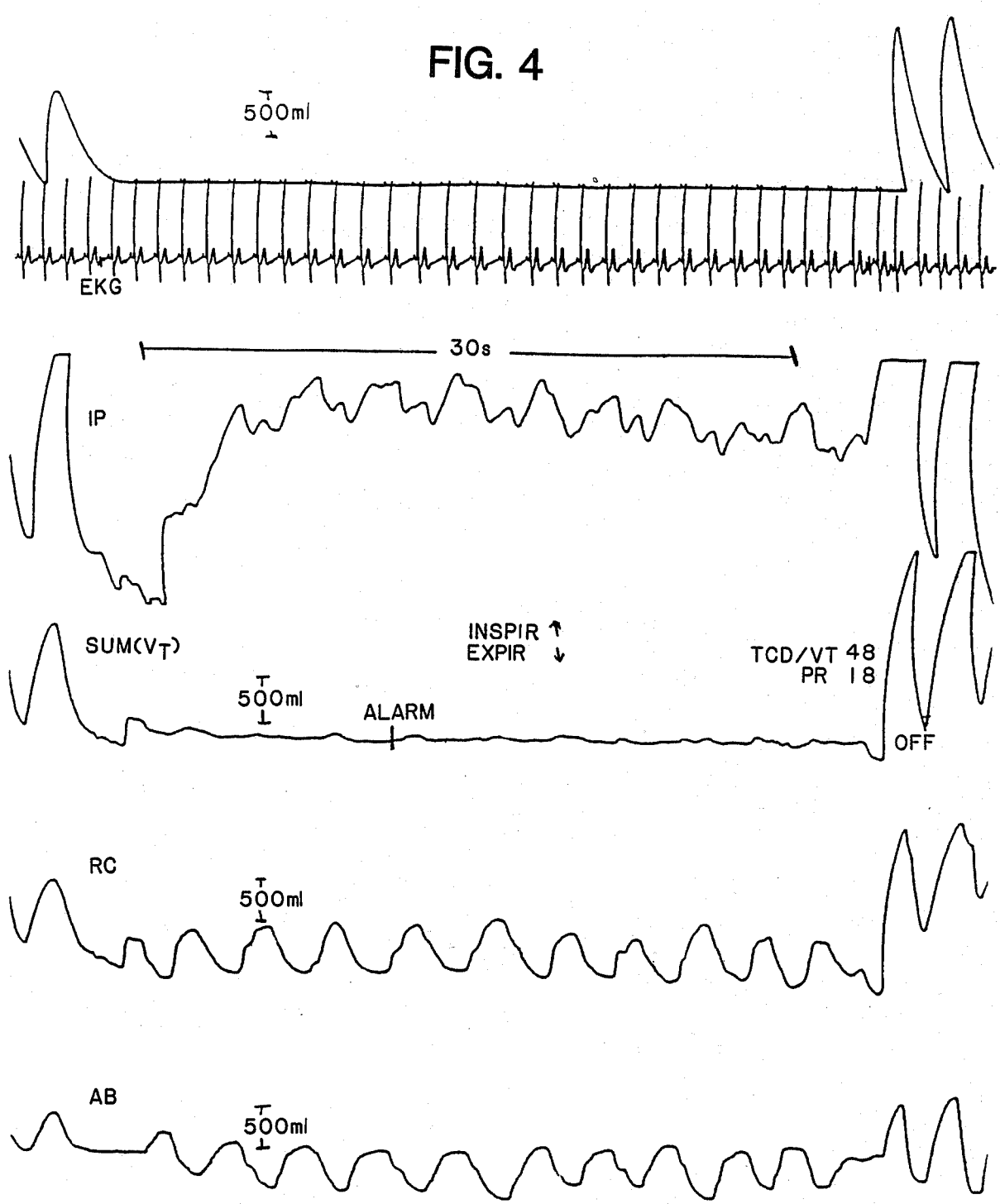
FIG. 4 is a polygraphic recording further illustrating the detection of obstructive apnea in accordance with the present invention.

FIG. 4 is a polygraphic recording from a simulation carried out by a normal volunteer. See the description of FIG. 3 for the legend designations. During the apnea as reflected by the flat tracing of SP and the minimal oscillations of SUM (VT), there are large RC and AB ccmpartmental displacements which are completely out-of-phase. These paradoxical movements of RC and AB produce a TCD/VT of 48 and PR of 18, values consistent with obstructive apnea. It should be noted that an apnea alarm sounds from the RESPIGRAPH TM but not with the impedance pneumograph since deflections during the obstructive apnea are recognized by this device as breaths, which would occur with any device which monitors only one compartment of the respiratory system.

Mixed Apnea

Figure 5:
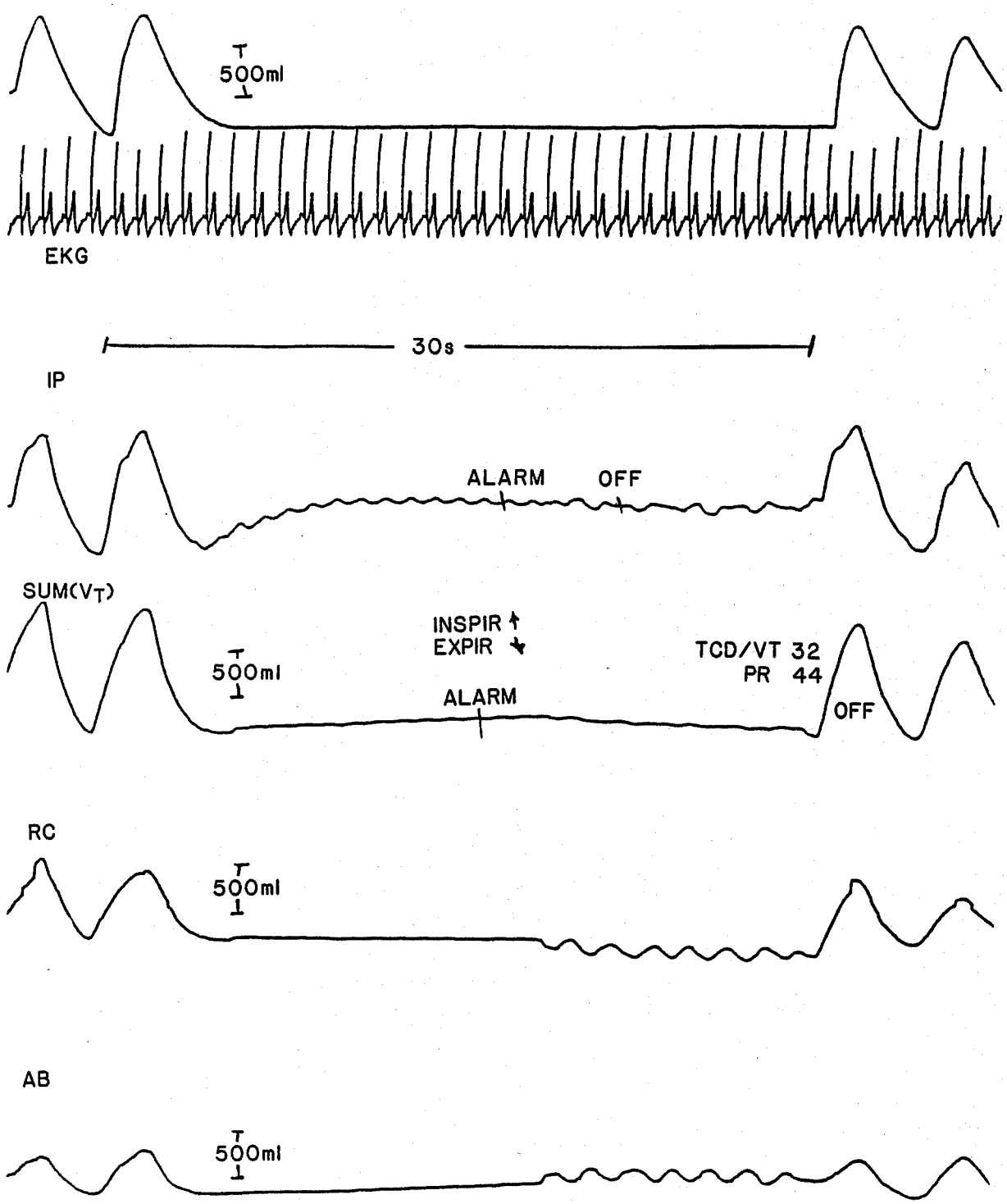
FIG. 5 is a polygraphic recording illustrating the detection of mixed apnea in accordance with the present invention.

FIG. 5 is a polygraphic recording similar to FIG. 3 from a simulation carried out by a normal volunteer. Refer to the discussion of FIG. 3 above for legend designations. The event here begins with a central apnea and is then followed by an obstructive apnea. The TCD/VT of 32 and PR of 44 are consistent with the diagnosis of a mixed apnea.

Despite the accuracy of the results reported above, and as noted earlier, it was subsequently determined that the foregoing technique does not discriminate among the various types of apneas with sufficient accuracy in all cases, and it has been found that apneas can be more accurately discriminated by visually inspecting compressed graphic plot lines for TCD and SUM (VT). The following specific examples pertain to this latter technique.

Central Apneas

Figure 6:
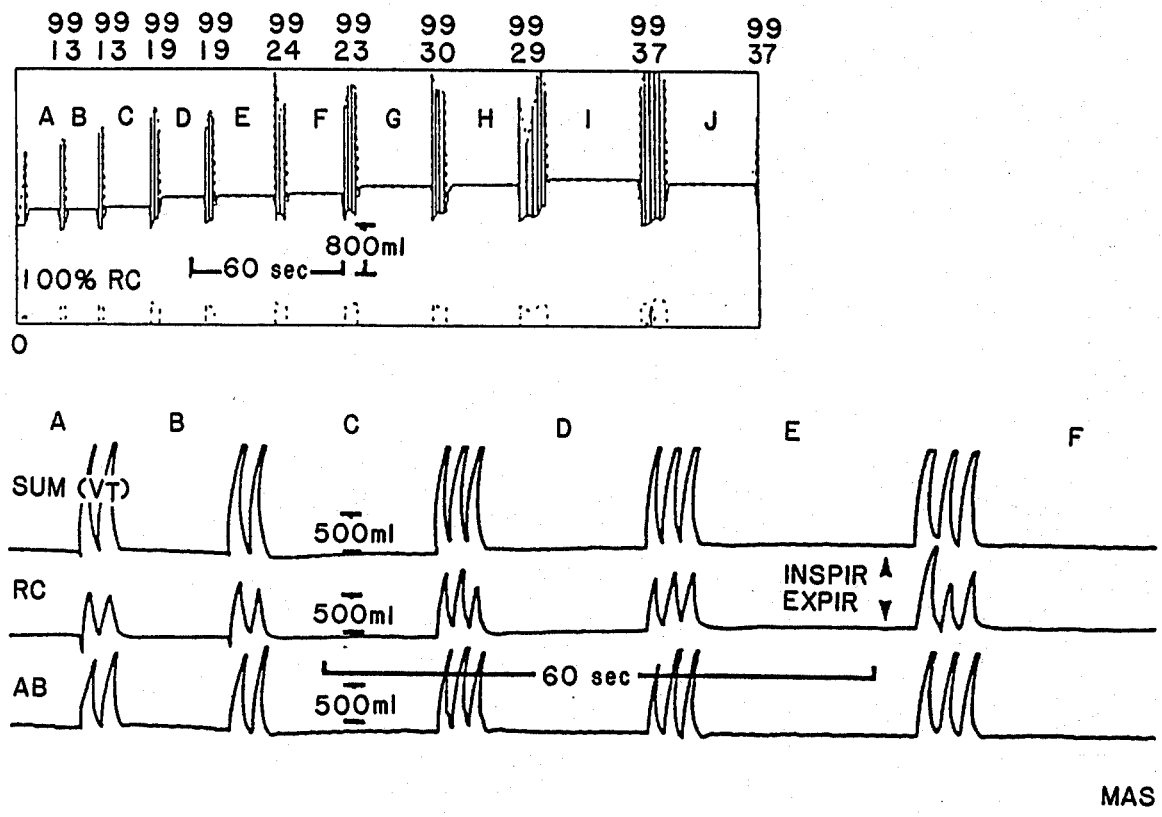
FIG. 6 is a compressed graphic plot (upper panel) in accordance with another aspect of the present invention depicting a series of central apneic events shown together with an analog recording (lower panel) of the SUM (VT), rib cage (RC) and abdominal (AB) signals.

The top panel in FIG. 6 depicts a series of central apneic events A-J on a compressed graphic plot generated by the RESPIGRAPH TM. The lower panel in FIG. 6 shows an analog recording of the SUM (VT), RC and AB signals as generated by RESPIGRAPH TM and recorded on a polygraph. The letters A, B, C, etc. in the lower panel indicate the correspondence between the apneic events depicted in the upper and the lower panels. As seen in FIG. 6, a total of ten central apneic events are depicted in the upper panel, and the first six of those are shown in the lower panel.

As indicated earlier, the termination of each apneic event as determined by the criteria mentioned above is indicated in the compressed plot (upper panel) by two numbers. The upper number, which is 99 in the case of each apneic event depicted in FIG. 6, indicates PR as a percentage. The lower number signifies the duration of the apneic event. As seen in FIG. 6, the apneic events range in duration from 13-37 seconds. The vertical lines between apneic events in the upper panel and the corresponing saw tooth wave form between apneic events in the lower panel represent normal breaths, e.g. two normal breaths between apneic events B and C, and three normal breaths between apneic events C and D, D and E, and E and F.

In all the compressed graphic plots of FIGS. 6-17, the solid line is the SUM (VT) signal and the hatched line is the TCD signal. As seen in the compressed graphic plot of FIG. 6 (upper panel), in each of the ten apneic events depicted, the SUM (VT) line is horizontal and only very slightly above the hatched TCD line, which is also horizontal. This indicates that all the apneic events are central apneas. As noted earlier, the hatched TCD line is slightly below the SUM (VT) line due to computer rounding errors.

As seen in the analog recordings in the lower panel of FIG. 6, the SUM (VT), RC and AB tracings are all flat during the apneic events, which confirms that each of the apneic events is in fact a central apneic event. The analog recordings are shown for purposes of comparison only, it being contemplated that during practice of the invention, only the compressed graphic plot (upper panel) will be visually inspected for discriminating among apneic events, though of course the analog recordings could also be displayed and reviewed.

Figure 7:
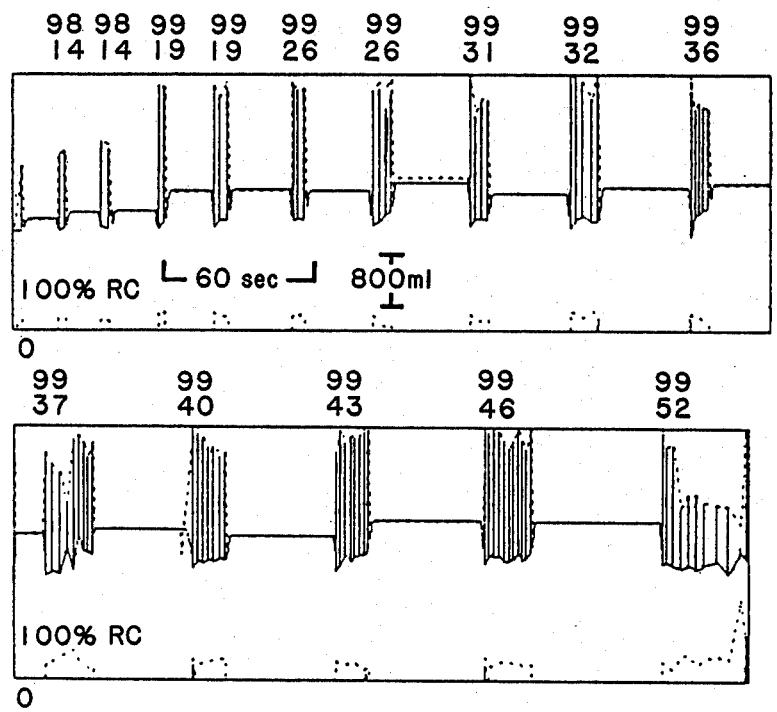
FIG. 7 is a compressed graphic plot similar to the compressed graphic plot in the upper panel of FIG. 1 showing another series of central apneic events.

FIG. 7 depicts a further series of central apneas in a compressed graphic plot. In FIG. 7, the lower compressed graphic plot is a continuation of the upper compressed graphic plot. As can be seen from FIG. 7, each apneic event is characterized by a solid, horizontal SUM (VT) line superimposed on or slightly displaced from a hatched, horizontal TCD line. Again, this idicates that each apneic event is a central apneic event. The numbers indicating the termination of each apneic event have the same significance as in FIG. 6.

Obstructive Apneas

Figure 8:
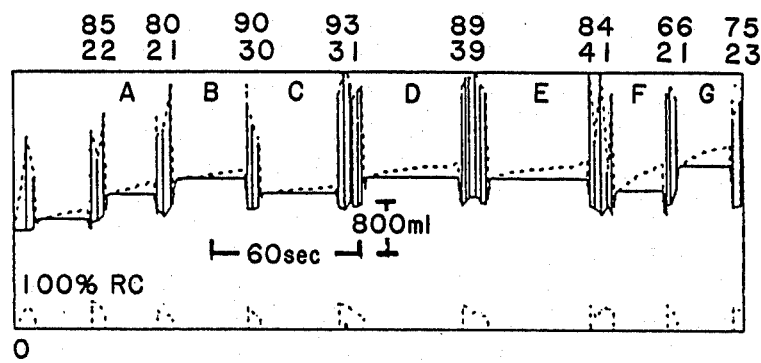
FIG. 8 is similar to FIG. 6 and shows a compressed graphic plot and corresponding analog recordings for a series of obstructive apneic events.
Figure 8:
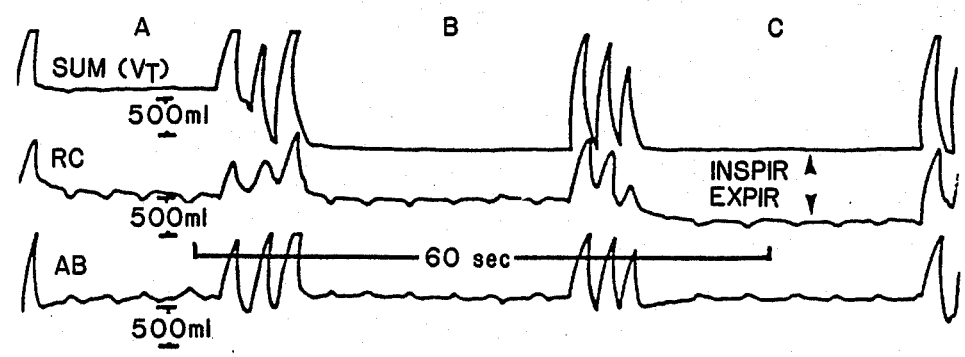

FIG. 8 depicts, in the upper panel, a compressed graphic plot showing a series of apneic events designated A-G. The lower panel of FIG. 8 shows analog recordings for the SUM (VT), RC and AB signals corresponding to the first three apneic events, A-C. The numerical values depicted above the compressed graphic plot have the same significance as in FIGS. 6 and 7, and this is true of all the compressed graphic plots of FIGS. 6-17.

As shown in the upper panel of FIG. 8, PR for the apneic events A-G ranges from 80-93 and the duration of the apneic events ranges from 21-41 seconds. Each apneic event A-G in the upper panel of FIG. 8 is characterized by a solid, horizontal SUM (VT) line and a hatched TCD line which angles upwardly and away from the SUM (VT) line. As noted earlier, this particular combination of a solid, horizontal SUM (VT) line and a hatched TCD line angling upwardly and awa from the SUM (VT) line indicates an obstructive apnea. This is confirmed by a PR of less than 97 for each of the apneic events A-G.

As can be seen in the lower panel of FIG. 8, the analog recordings for the SUM (VT), RC and AB signals confirm that the apneic events A-C are in fact obstructive apneic events. This is apparent from the RC and AB components which depict respiratory effort with the RC and AB components being substantially out of phase.

Figure 9:
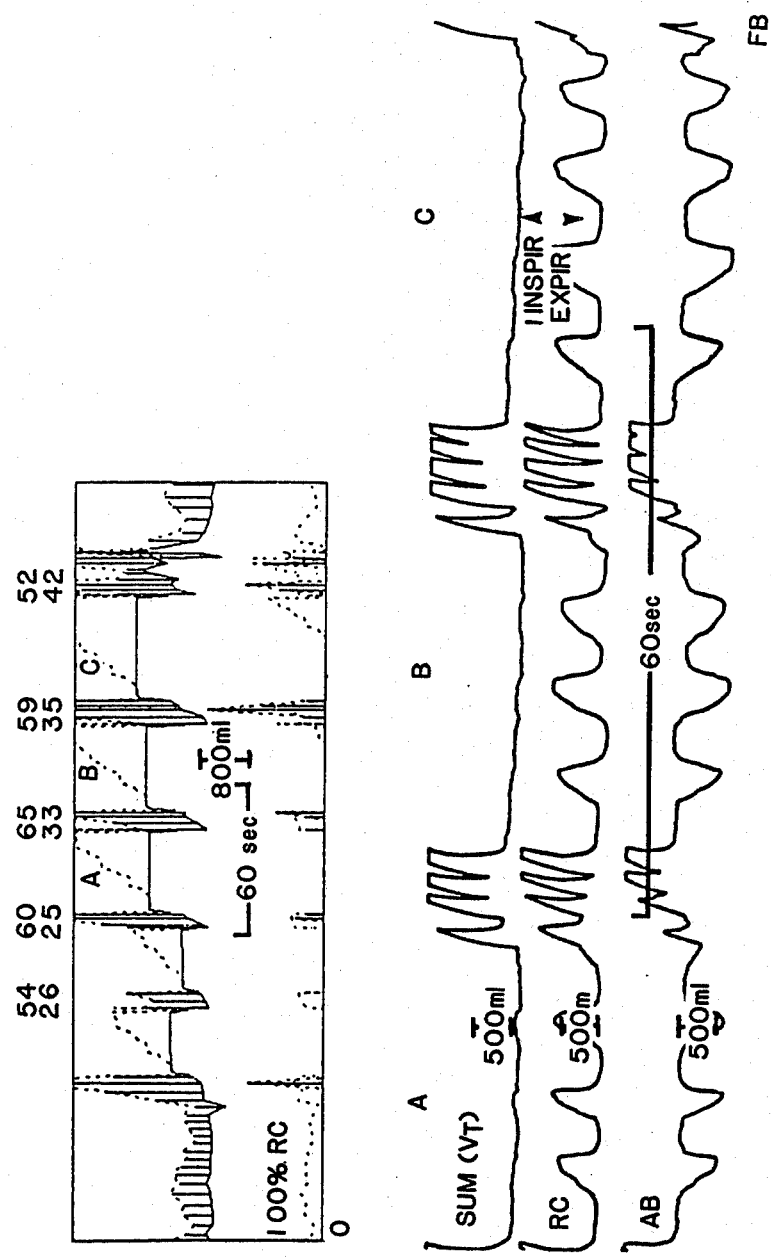
FIG. 9 is also similar to FIG. 6 and shows a compressed graphic plot and corresponding analog recordings showing another series of obstructive apneic events.

The upper panel of FIG. 9 is a compressed graphic plot showing a further series of obstructive apneic events, three of which are designated A-C. As before, the lower panel shows the analog recordings for the SUM (VT), RC and AB signals for the apneic events A, B and C as recorded on a polygraph.

Note that in the compressed graphic plot in the upper panel, each of the apneic events A-C has the visual appearance indicative of an obstructive apneic event, namely, a solid, horizontal SUM (VT) line and a hatched TCD line sloping upwardly and away from the SUM (VT) line. The steep angle of the hatched TCD line indicates marked respiratory efforts, and this is confirmed by the large, out of phase deflections between the RC and AB components in the analog recordings shown in the lower panel. In the graphic plot, the rise in the hatched TCD line is so steep that the tracing wraps around the top of the plot and continues to rise as it reenters on the bottom of the plot. See particularly the apneic event designated C. Note that PR for each of the apneic events is well below 97 which, as noted earlier, is also consistent with obstructive apneic events.

Figure 10:
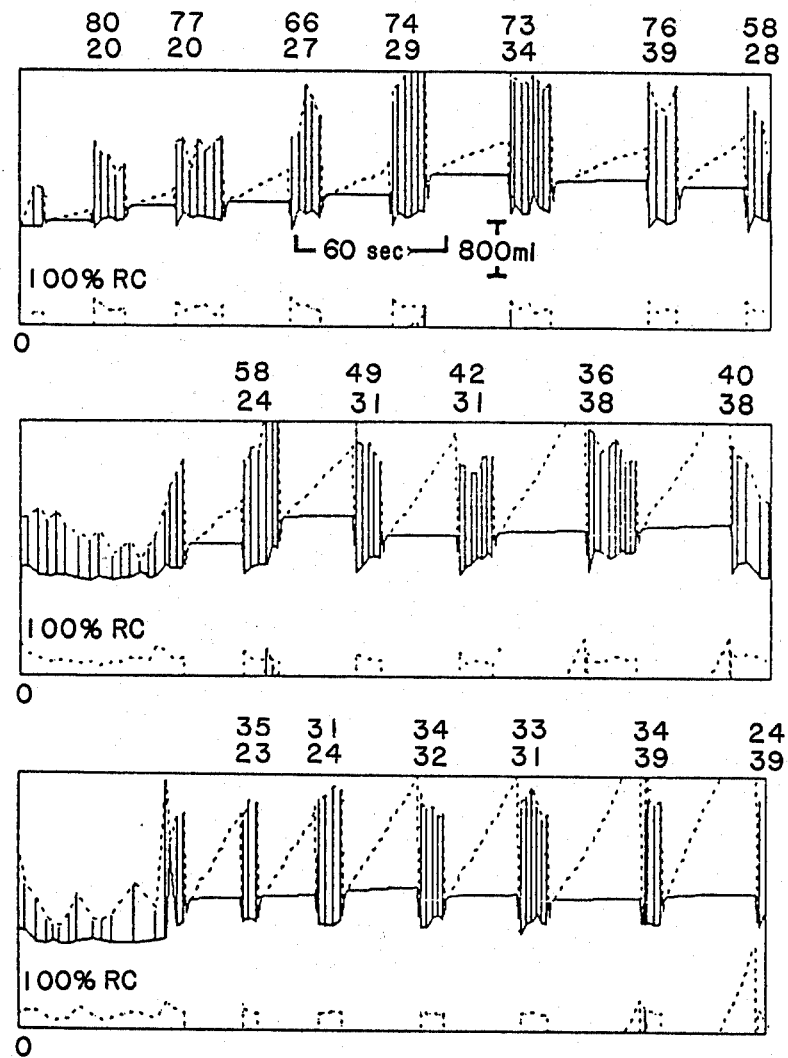
FIG. 10 shows a compressed graphic plot in three panels showing still another series of obstructive apneic events.

FIG. 10 shows a further series of obstructive apnea in a compressed graphic plot. While the graphic plot is shown in three sections due to space limitations, in fact it is a continuous graphic plot beginning with the upper panel and ending with the bottom panel. Note that each of the apneic events depicted in FIG. 10 is consistent with an obstructive apneic event according to the visual criteria mentioned above. In FIG. 10, the obstructive apneic events demonstrate increasing intensity of respiratory effort as indicated by the increasingly steep rise of the hatched TCD line. This is further confirmed by the diminishing value of PR which decreases from 80 for the obstructive apneic event at the left of the upper panel to 24 for the obstructive apneic event at the right of the bottom panel.

Mixed Apneas

Figure 11:
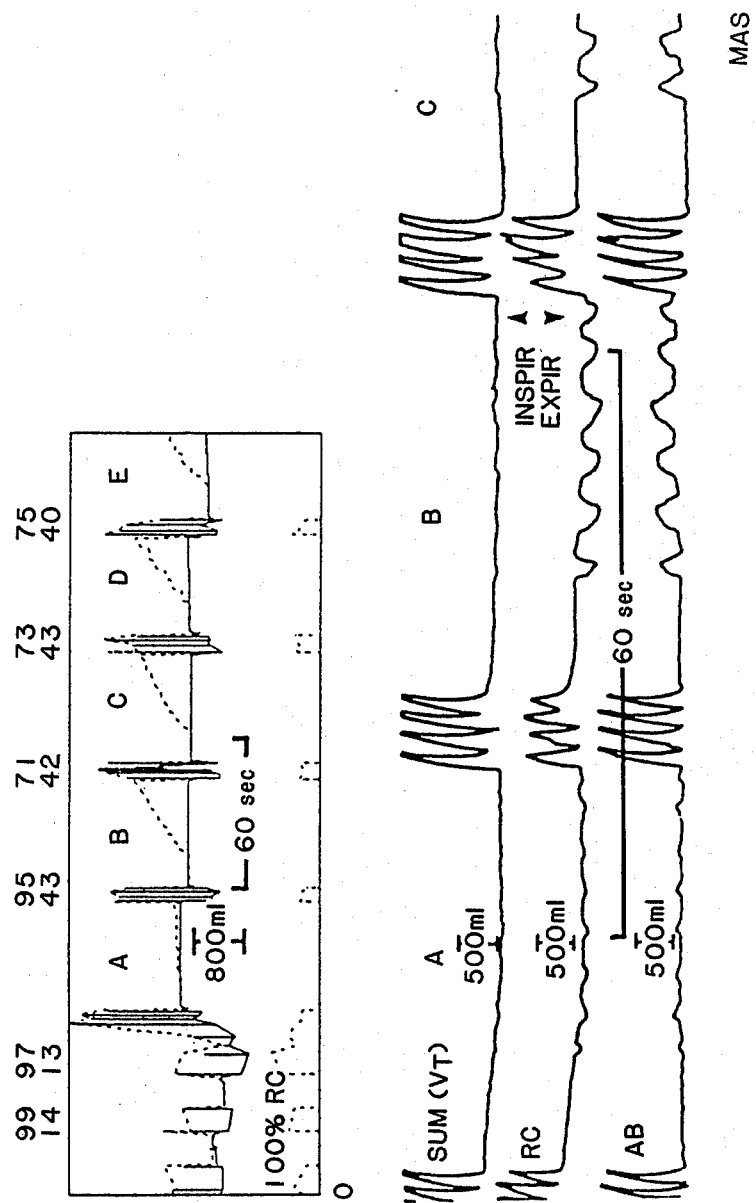
FIG. 11 is similar to FIG. 6 and shows a compressed graphic plot and corresponding analog recordings for a series of mixed apneic events.

FIG. 11 shows in the upper panel a compressed graphic plot depicting a series of mixed apneas designated A-E. The lower panel in FIG. 11 shows the analog recordings for the SUM (VT), RC and AB signals for the apneic events A-C as recorded on a polygraph.

Each mixed apneic event is characterized by a first portion wherein the SUM (VT) signal and the TCD signal are horizontal and superimposed or slightly displaced, and a second component wherein the TCD line slopes upwardly and away from the SUM (VT) line. In accordance with the visual criteria established above, the first component of each apneic event is indicative of a central apnea and the second component is indicative of an obstructive apnea. Consequently, each apneic event is a true mixed apneic event.

As indiated by the steeper slope of the TCD line in apneic events B-E as compared with event A, apneic events B-E depict increasing respiratory effort during the obstructive phase as compared with apneic event A. This is confirmed in the lower panel by the increasing amplitude of the RC and AB components during events B and C. Note that PR for each of the apneic events is less than 97, which is also consistent with mixed apneic events.

Figure 12:
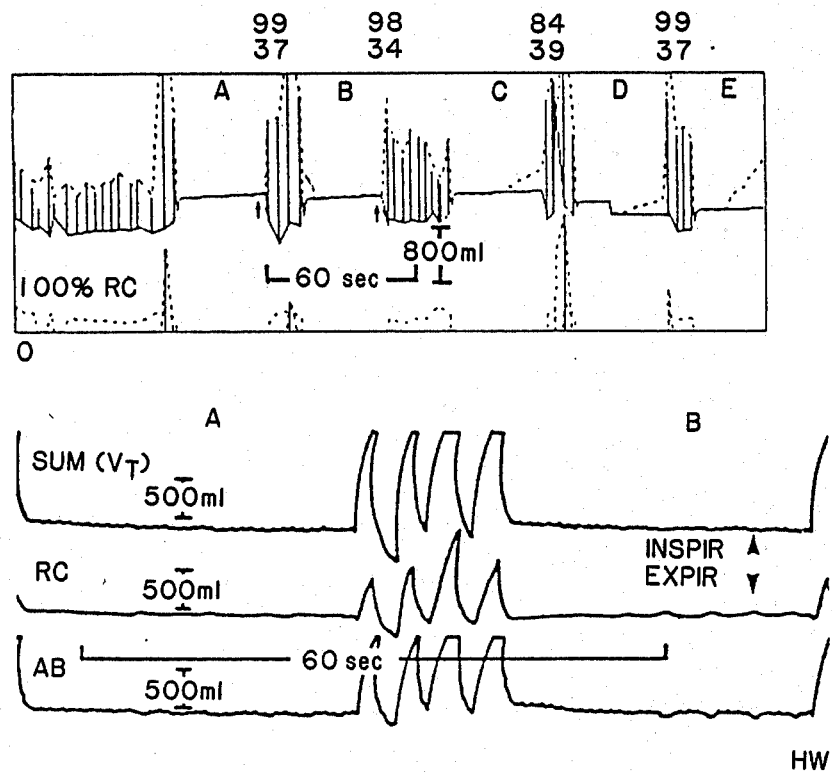
FIG. 12 is also similar to FIG. 6 and also shows a compressed graphic plot and corresponding analog recordings for a series of mixed apneic events.

FIG. 12 shows in the upper panel a series of mixed apneic events designated A-E, and the lower panel shows the analog recordings for the SUM (VT), RC and AB components for events A and B. Note that for apneic events A and B, PR is 99 and 98, respectively, which is indicative of a central apneic event, but this is contradicted by the slight upward rise of the hatched TCD line during the end of each of the apneic events A and B, which reflects an obtructive apneic component. The arrows in the compressed graphic plot at the end of apneic events A and B indicate this slight upward rise of the hatched TCD line at the end of these apneic events, which is somewhat difficult to see in FIG. 12. Note that the obstructive component is confirmed by the analog recordings. For example, for apneic event B, the minimal respiratory effort during the obstructive phase is indicated by the out of phase movement of the RC and AB components. The rapid, low amplitude oscillations on the SUM (VT) and AB recordings in the lower panel result from transmission of the heartbeat to the AB transducer.

Figure 13:
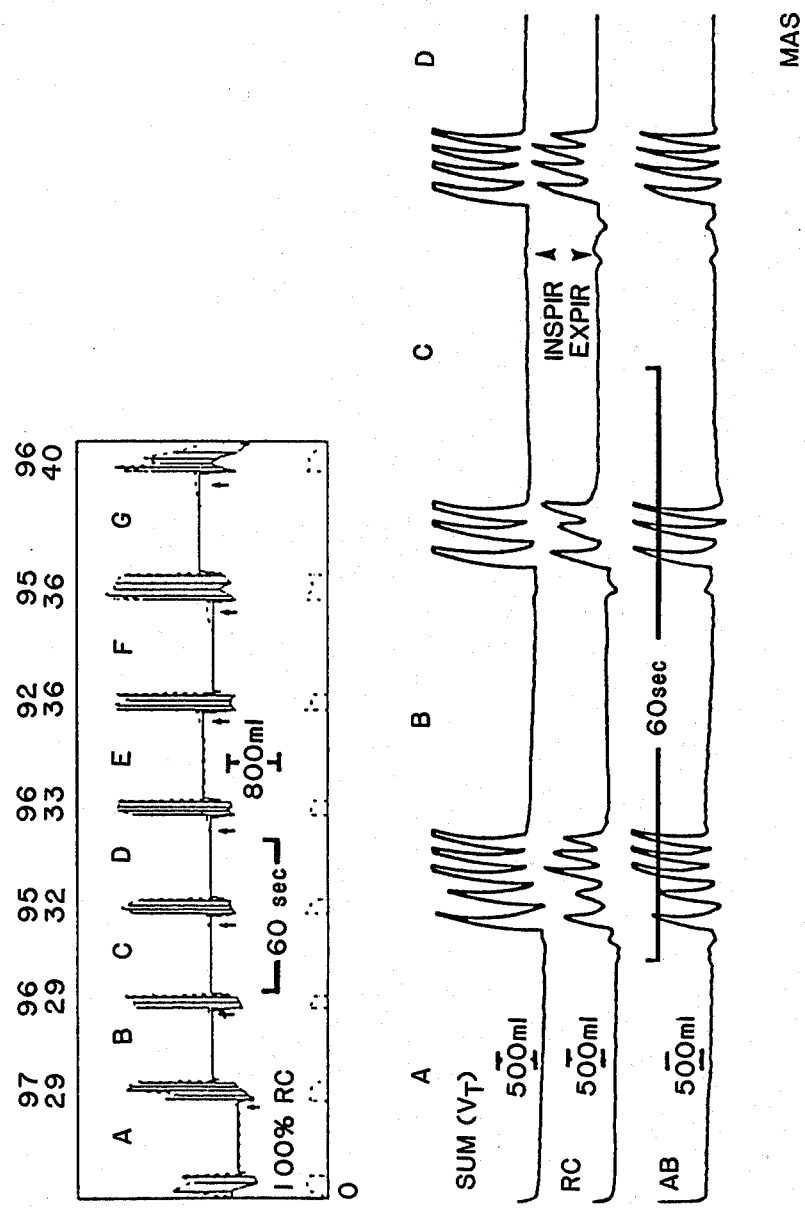
FIG. 13 is also similar to FIG. 6 and also shows a compressed graphic plot and corresponding analog recordings for another series of mixed apneic events.

FIG. 13 illustrates an example where it would be difficult to discriminate between central and mixed apneas by relying solely on numerical values of TCD/VT and PR without visually inspecting the compressed graphic plot. In FIG. 13, the apneic events A and B each have a prolonged central apneic component terminating in a single obstructive breath with minimal respiratory effort. Apneic event C shows a prolonged central component terminating in two obstructive breaths. For each of the apneic events A-G shown in the compressed graphic plot, the arrows at the end of the apneic events indicate the obstructive component, which is characterized by a slight rise in the hatched TCD line above the SUM (VT) line. Note that the PR values of 92-97 approach those indicative of central apneas because of the relatively long duration of the central apneic components as compared with the obstructive components. Consequently, in situations such as this, it will be apparent that a visual inspection of the compressed graphic plot enables the viewer to more accurately classify the apneic event than would a reliance solely on numerical values for TCD/VT and PR.

Figure 14:
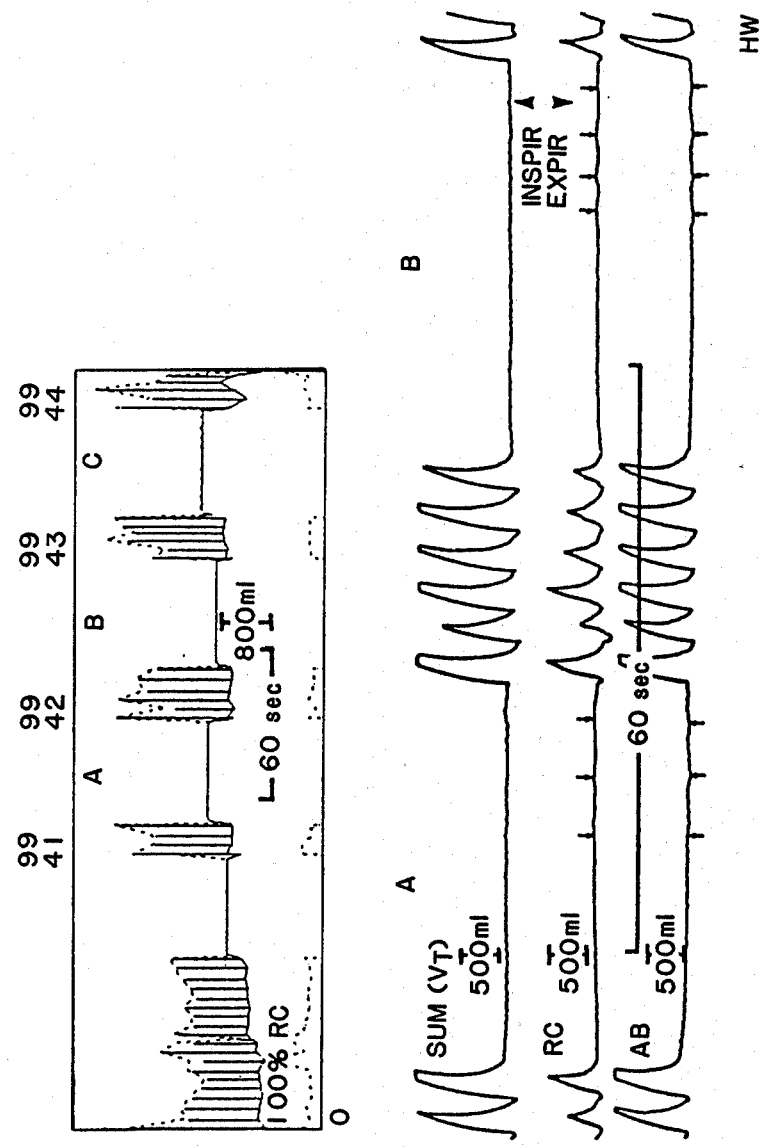
FIG. 14 is also similar to FIG. 6 and also shows a compressed graphic plot and corresponding analog recordings for a series of mixed apneic events.

FIG. 14 shows a mixed apnea with an obstructive component of very minimal respiratory effort. In fact, the respiratory effort during the obstructive component is so slight that it is not even apparent form visual inspection of the compressed graphic plot, as can be seen from the fact that the SUM (VT) and TCD lines for apneic events A, B and C are both horizontal and superimposed (apneic events A and B) or only slightly displaced (apneic event C). Consequently, one viewing the compressed graphic plot of FIG. 14 would interpret the apneic events A-C as central apneic events. However, and as is apparent from the RC and AB components depicted in the analog recordings in the lower panel, there is a minimal respiratory effort at the end of apneic events A and B as indicated by the arrows, there being three obstructive breaths at the end of apneic event A and four at the end of apneic event B. In this situation, i.e. a mixed apnea having an obstructive component typified by minimal respiratory effort, confidence in apnea discrimination can be enhanced by monitoring intrapleural pressure as by employing a surface inductive plethysmograph as is more fully explained above.

Figure 15:
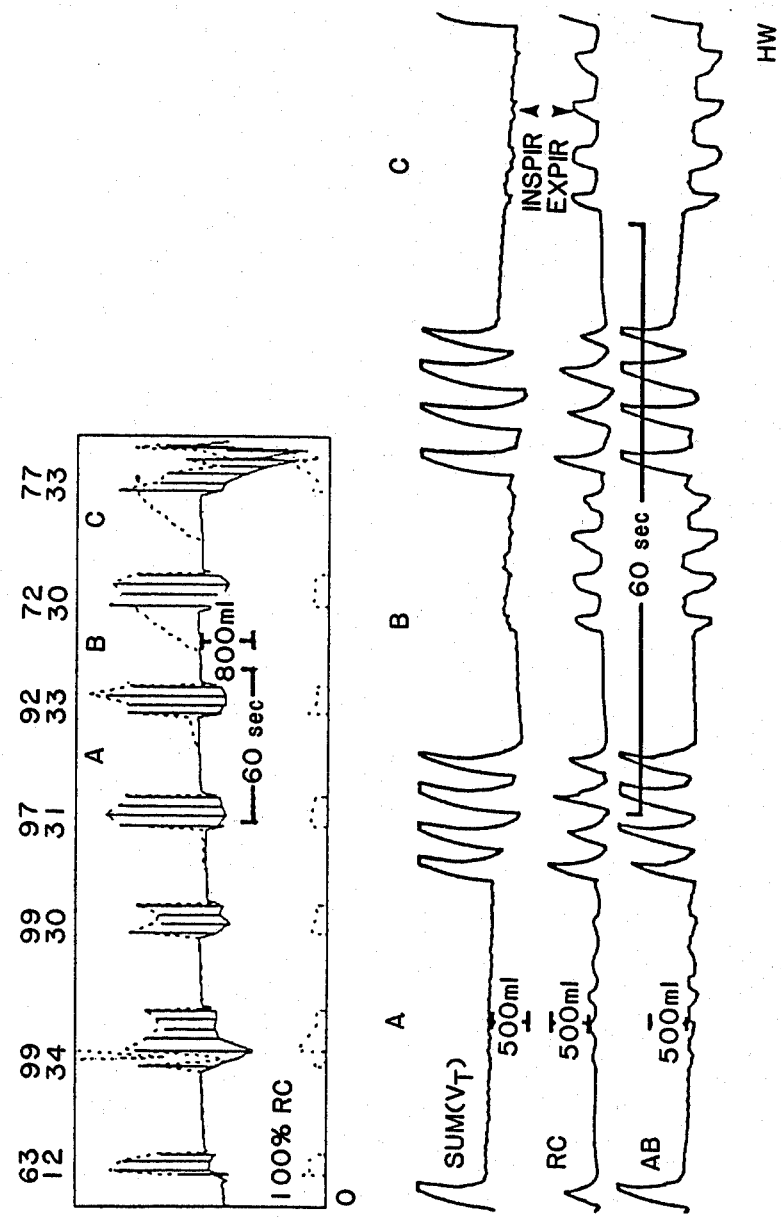
FIG. 15 is also similar to FIG. 6 and also shows a compressed graphic plot and corresponding analog recordings for a series of mixed apneic events.

FIG. 15 shows three mixed apneic events A-C with event A exhibiting an obstructive component of minimal respiratory effort and events B and C depicting obstructive components of increasing respiratory effort.

Figure 16:
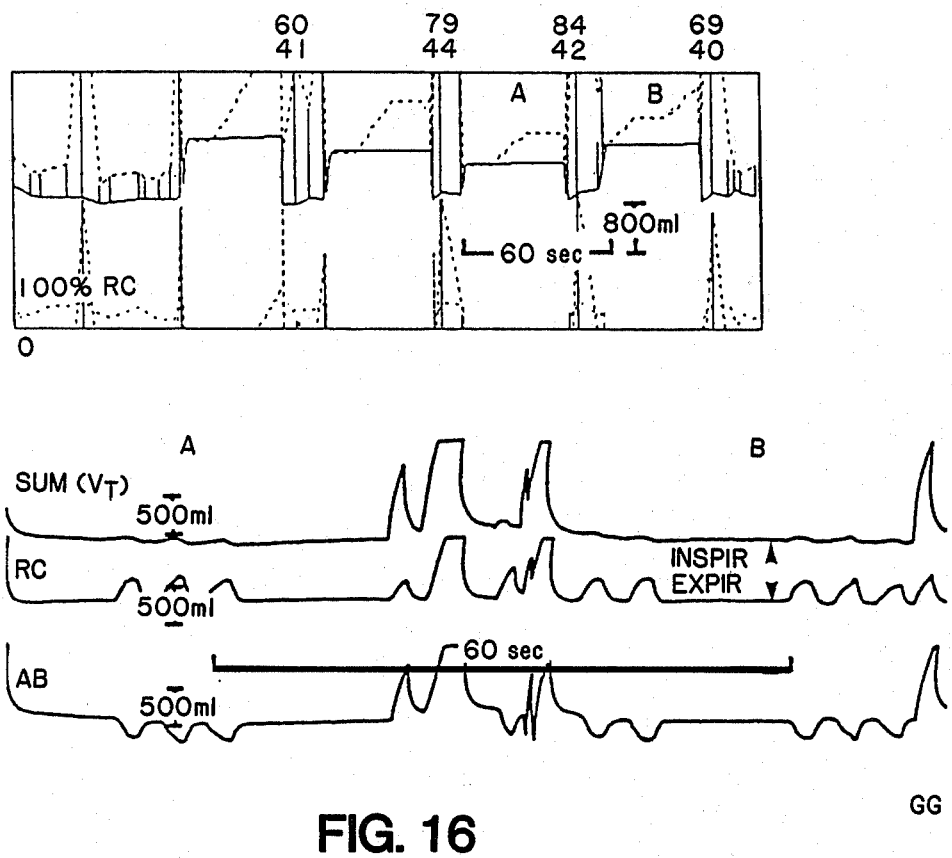
FIG. 16 is also similar to FIG. 6 and also shows a oompressed graphic plot corresponding analog recordings for a series of mixed apneic events.

FIG. 16 depicts two apneic events A and B. In event A, a central component is followed by an obstructive component and then by another central component. During the first central component, the SUM (VT) and TCD lines are both horizontal and substantially coincident, during the obstructive component the TCD line slopes upwardly and away from the SUM (VT) line, and during the second central component the TCD and SUM lines are parallel and displaced from each other. Apneic event B shows an obstructive component followed by a central component followed by another obstructive component. In this case, the TCD line rises, becomes flat again, and then rises again. The changing components of the apneic events A and B is confirmed by the analog recording shown in the lower panel of FIG. 16.

Figure 17:
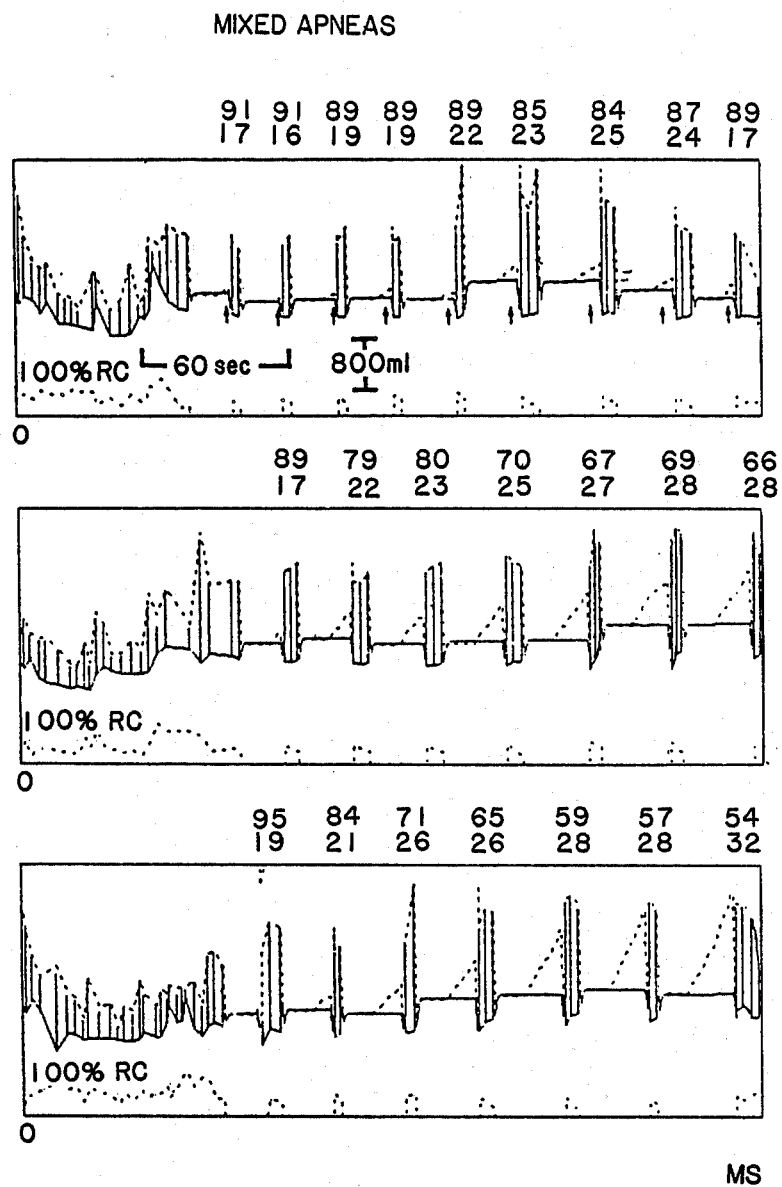
FIG. 17 is also similar to FIG. 6 and also shows a compressed graphic plot and corresponding analog recordings for a series of mixed apneic event.
Figure 18:
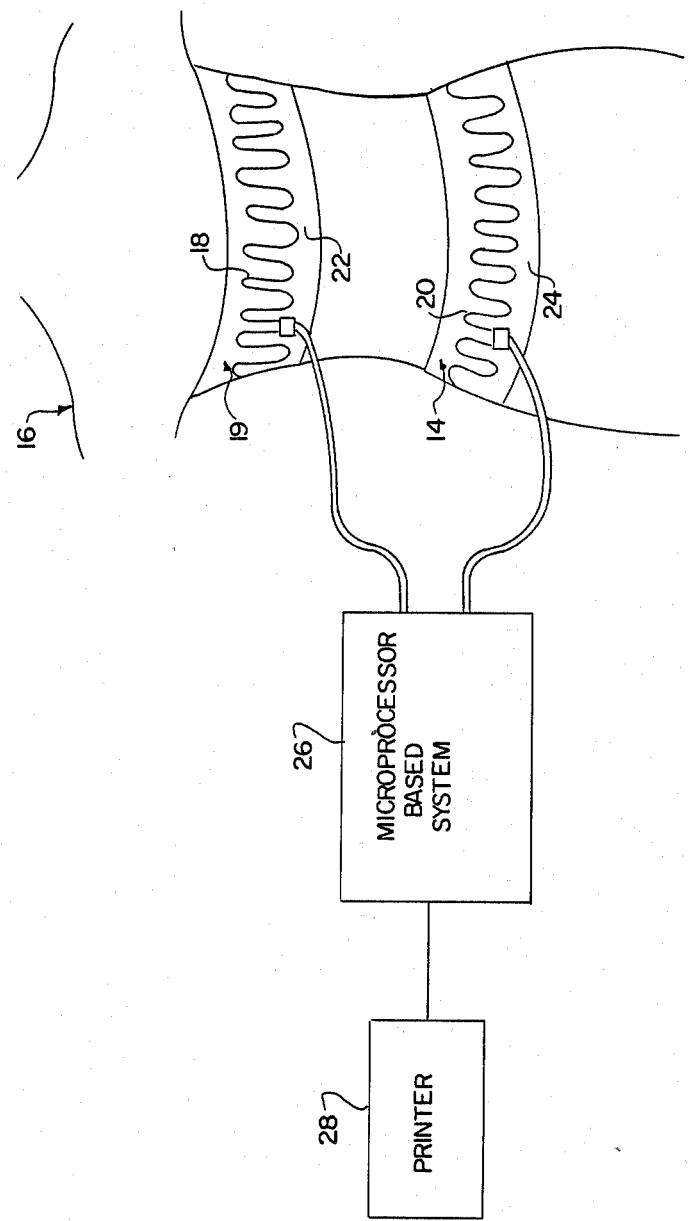
FIG. 18 is a diagrammatic illustration of a suitable apparatus for practicing the method of the present invention.

FIG. 17 is a compressed graphic plot showing a series of mixed apneic events exhibiting varying degrees of respiratory effort ranging from minimal, to moderate, to marked for the obstructive component. Note that the PR values fall from a high of 91% for the apneic event at the left of the upper panel to 54% for the apneic event at the right of the bottom panel.

What is claimed is:

1. A method for differentiating among central, obstructive and mixed apneas in a subject comprising
    (a) determining the existence of an apneic event;
    (b) measuring TCD during said apneic event and providing a signal indicative thereof;
    (c) measuring SUM (VT) during said apneic event and providing a signal indicative thereof;
    (d) displaying said TCD and SUM (VT) signals on a compressed plot;
    (e) classifying said event as a central apneic event when said displayed TCD and SUM (VT) signals are coincident or parallel;
    (f) classifying said event as an obstructive apneic event when said displayed TCD signal slopes at an angle from said displayed SUM (VT) signal during substantially said entire apneic event; and
    (g) classifying said event as a mixed apneic event when said displayed SUM (VT) and TCD signals are coincident or parallel for a portion of said apneic event and said displayed TCD signal slopes away from said SUM (VT) signal during another portion of said apneic event.

2. The method according to claim 1, further comprising measuring PR during said apneic event and confirming the classification of said apneic event as a central apneic event if PR is about 98 to about 99, confirming said apneic event as an obstructive apneic event if PR is less than about 97, and confirming said apneic event as a mixed apneic event if PR is less than about 97.

3. The method according to claim 1, further comprising measuring intrapleural pressure during said apneic event and confirming classification of said event or a component thereof as a central apnea if no changes in intrapleural pressure are recorded during said event or said component thereof, respectively, and confirming classification of said event or a component thereof as an obstructive apnea if a change in intrapleural pressure is recorded during said event or said component thereof, respectively.

4. The method according to claim 2, further comprising measuring intrapleural pressure during said apneic event and confirming classification of said event or a component thereof as a central apnea if no changes in intrapleural pressure are recorded during said event or said component thereof, respectively, and confirming classification of said event or a component thereof as an obstructive apnea if a change in intrapleural pressure is recorded during said event or said component thereof, respectively.

5. A method for differentiating among central, obstructive and mixed apneas in a subject comprising
    (a) determining the existence of an apneic event;
    (b) measuring TCD/VT during said apneic event;
    (c) measuring PR during said apneic event;
    (d) classifying the apneic event as central, obstructive or mixed based on the measured values for TCD/VT and PR according to the following criteria:

| TCD/VT (× 10) | PR (× 100) | Type of Apnea |
| --- | --- | --- |
| about 10–about 15 | > about 50 | Central |
|  | ≦ about 50 | Mixed |
| about 16–about 19 | > about 50 | Central |
|  | about 40–about 49 | Mixed |
|  | < about 39 | Obstructive |
| about 20–about 25 | ≧ about 55 | Central |
|  | < about 55 | Mixed or Obstructive |
| ≧ about 25 | > about 60 | Central |
|  | about 40–about 59 | Mixed |

-continued

| TCD/VT (× 10) | PR (× 100) | Type of Apnea |
| --- | --- | --- |
| | < about 39 | Obstructive |

6. The method according to claim 1, further comprising measuring intrapleural pressure during said apneic event and confirming classification of said event or a component thereof as a central apnea if no changes in intrapleural pressure are recorded during said event or said component thereof, respectively, and confirming classification of said event or a component thereof as an obstructive apnea if a change in intrapleural is recorded during said event or said component thereof, respectively.

7. An apparatus for differentiating among central, obstructive and mixed apneas in a subject comprising
   (a) means for determining the existence of an apneic event;
   (b) means for measuring TCD/VT during said apneic event;
   (c) means for measuring PR during said apneic event;
   (d) means for classifying the apneic event as central, obstructive or mixed based on the measured values for TCD/VT and PR according to the following criteria:

| TCD/VT (× 10) | PR (× 100) | Type of Apnea |
| --- | --- | --- |
| about 10–about 15 | > about 50 | Central |
| | ≦ about 50 | Mixed |
| about 16–about 19 | > about 50 | Central |
| | about 40–about 49 | Mixed |
| | < about 39 | Obstructive |
| about 20–about 25 | ≧ about 55 | Central |
| | < about 55 | Mixed or Obstructive |

8. The apparatus according to claim 2, further comprising means for measuring intrapleural pressure during said apneic event for confirming classification of said event or a component thereof as a central apnea if no changes in intrapleural pressure are recorded during said event or said component thereof, respectively, and confirming classification of said event or component thereof as an obstructive apnea if a change in intrapleural pressure is recorded during said event or said component thereof, respectively.

9. An apparatus for differentiating among central, obstructive and mixed apeneas in a subject comprising (a) means for determining the existence of an apneic event; (b) means for measuring TCD during said apneic event and providing a signal indicative thereof; (c) means for measuring the SUM (VT) during said apneic event and providing a sigal indicative thereof; (d) means for detecting the slopes of said TCD and SUM (VT) signals; and (e) means for classifying an event as a central apneic event when the slopes of said TCD and SUM (VT) signals are substantially the same, as an obstructive apneic event when the slope of said TCD signal is different from the slope of said SUM (VT) signal during substantially said entire apneic event, and as a mixed apneic event when the slopes of said TCD and SUM (VT) signals are substantially the same for a portion of said apneic event and the slope of said TCD signal is different from the slope of said SUM (VT) signal during another portion of said apneic event.

10. The apparatus according to claim 9, further comprising means for measuring PR during said apneic event and means for confirming the classification of said apneic event as a central apneic event if PR is about 98 to about 99, and means for confirming said apneic event as an obstructive apneic event if PR is less than about 97, and confirming said apneic event as a mixed apneic event if PR is less than about 97.

11. The apparatus according to claim 9, further comprising means for measuring intrapleural pressure during said apneic event and means for confirming classification of said event or a component thereof as a central apnea if no changes in intrapleural pressure are recorded during said event or said component thereof, respectively, and means for confirming classification of said event or a component thereof as an obstructive apnea if a change in intrapleural pressure is recorded during said event or said component thereof, respectively.

12. The apparatus according to claim 10, further comprising means for measuring intrapleural pressure during said apneic event and means for confirming classification of said event or a component thereof as a central apnea if no changes in intrapleural pressure are recorded during said event or said component thereof, respectively, and means for confirming classification of said event or a component thereof as an obstructive apnea if a change in intrapleural pressure is recorded during said event or said component thereof, respectively.

* * * * *

UNITED STATES PATENT AND TRADEMARK OFFICE
CERTIFICATE OF CORRECTION

PATENT NO. : 4,777,962

DATED : Oct. 18, 1988

INVENTOR(S) : Watson et al

It is certified that error appears in the above-identified patent and that said Letters Patent is hereby corrected as shown below:

Column 7, line 42, delete "and"; and
        line 45, "event; and" should be --events; and--.

Column 16, line 7, "sigal" should be --signal--.

Signed and Sealed this

Eighteenth Day of February, 1992

Attest:

HARRY F. MANBECK, JR.

*Attesting Officer*        *Commissioner of Patents and Trademarks*